US012746310B2

(12) United States Patent
Lou

(10) Patent No.: US 12,746,310 B2
(45) Date of Patent: Sep. 29, 2026

(54) BREAST PUMPING SYSTEM

(71) Applicant: Ningbo Huiyoo Baby Products Co., Ltd., Cixi (CN)

(72) Inventor: Zongguo Lou, Cixi (CN)

(73) Assignee: Ningbo Huiyoo Baby Products Co., Ltd., Cixi (CN)

( * ) Notice: Subject to any disclaimer, the term of this patent is extended or adjusted under 35 U.S.C. 154(b) by 425 days.

(21) Appl. No.: 18/505,537

(22) Filed: Nov. 9, 2023

(65) Prior Publication Data

US 2025/0090732 A1 Mar. 20, 2025

(30) Foreign Application Priority Data

Sep. 19, 2023 (CN) ......................... 202311213973.9

(51) Int. Cl.
*A61M 1/06* (2006.01)

(52) U.S. Cl.
CPC .................................. *A61M 1/062* (2014.02)

(58) Field of Classification Search
CPC ...... A61M 1/06; A61M 1/069; A61M 1/0693; A61M 1/06935; A61M 1/062; A61M 1/067
See application file for complete search history.

(56) References Cited

U.S. PATENT DOCUMENTS 11,554,199 B1 * 1/2023 Chen ........................ A61M 1/06
2018/0008758 A1 * 1/2018 Garbez ................. A61M 39/22
2018/0104396 A1 * 4/2018 Park ....................... A61M 1/066
2023/0347026 A1 * 11/2023 Luo .......................... A61M 1/06
2023/0364310 A1 * 11/2023 Luo ........................ A61M 1/064
2024/0001009 A1 * 1/2024 Chen ...................... A61M 1/062
2024/0399035 A1 * 12/2024 Chen ........................ A61M 1/73

FOREIGN PATENT DOCUMENTS

CN 215386356 U * 1/2022 .............. A61M 1/06
CN 218589446 U * 3/2023
CN 116378927 A * 7/2023 ............ A61M 1/062
CN 116650742 A * 8/2023 .............. A61M 1/06
CN 219462081 U * 8/2023 .............. A61M 1/06

* cited by examiner

*Primary Examiner* — William R Carpenter
(74) *Attorney, Agent, or Firm* — Wang Law Firm, Inc.

(57) ABSTRACT

The present invention discloses a breast pumping system comprising a housing, an air pump, a milk container, a pipe, a diaphragm, a shield and a cover, wherein, when the air pump acts on the air chamber through the vent pipe, the diaphragm is distorted so as to form a negative pressure inside the receiving chamber of the pipe, accordingly the milk from the passage flows into the storing chamber of the milk container after passing through the receiving chamber and the lower port successively. The air chamber can be manufactured larger in size so as to improve the pumping effect of the breast pump. When the air pump is an air pump with large pumping force, the pumping power can be further increased, and the pumping effect of the breast pump can be improved. The diaphragm is directly sealed to the cover, so that the sealing effect is good, it is not easy to cause air leakage, and the structure is reasonable and reliable.

7 Claims, 11 Drawing Sheets

BREAST PUMPING SYSTEM

TECHNICAL FIELD OF THE INVENTION

The present invention relates to a field of breast pumping devices, and in particular to a breast pumping system.

BACKGROUND OF THE INVENTION

The breast pumping system is used to pump out milk. The breast pumping system generally comprises an air pump and a milk container, wherein the air pump operates to generate negative pressure, and the milk is pumped into the milk container under the action of the negative pressure.

For example, a Chinese Patent CN213964594U (patent No.: CN201890000923.9) discloses a breast pumping system, wherein the breast pumping system comprises a housing partially fitting inside a bra and a piezo air-pump; the piezo air-pump is arranged in the housing and forms part of a closed loop system that drives a deformable diaphragm to generate negative air pressure; and the diaphragm is removably mounted on a breast shield.

However, the above patent has the following problems.

Firstly, in the above patent, the diaphragm is disc-shaped and fitted with a rear wall of the housing to form an air chamber, and the air chamber is small in size. In addition, the air pump is a piezo air-pump with a small size, and the pumping power of the piezo air-pump is relatively low, so that the pumping power of the breast pump is relatively low and the pumping effect will be affected.

Secondly, in the above patent, a flexible valve is used to resist against an opening of a nipple passage to realize self-sealing, and the self-sealed position has an inclined slope. When the shield is not mounted in place or the flexible valve is deformed after being used for a period of time, air leakage is easy to occur at the self-sealed position, so that the pumping effect of the breast pump will be affected.

SUMMARY OF THE INVENTION

It is a first object of the present invention to provide a novel breast pumping system with good pumping effect.

It is a second object of the present invention to provide a novel breast pumping system which is not easy to cause air leakage and has good pumping effect.

For achieving the first object, the breast pumping system comprises:

- a housing having a lower portion, a front side and a rear side;
- an air pump arranged in the housing;
- a milk container arranged at the lower portion of the housing, having a storing chamber with a rear opening;
- a pipe arranged inside the storing chamber of the milk container, having a front side, a receiving chamber, a top port, a middle port and a lower port, the top port, the middle port and the lower port communicating with the receiving chamber, the middle port facing backward, the lower port communicating with the storing chamber;
- a diaphragm arranged inside the receiving chamber of the pipe and located between the top port and the middle port;
- a shield having a passage facing backward for receiving a nipple, the passage communicating with the middle port of the pipe, the shield covering the rear opening of the milk container;
- a cover arranged inside the storing chamber and located at the top port of the pipe, an air chamber being defined between the cover and the diaphragm, the cover having a vent pipe communicating with the air chamber and the air pump;

wherein,

- the diaphragm is at least partially distortable in shape and is capable of isolating air from the vent pipe from milk inside the receiving chamber of the pipe;
- when the air pump acts on the air chamber through the vent pipe, the diaphragm is distorted so as to form a negative pressure inside the receiving chamber of the pipe, accordingly the milk from the passage flows into the storing chamber of the milk container after passing through the receiving chamber and the lower port successively.

For convenience of assembly and disassembly, preferably, the cover is detachably sealed to the diaphragm. In this way, it is convenient for assembly and disassembly, and the sealing effect between the cover and the diaphragm is ensured.

Preferably, the structure that facilitates the cover to detachably sealed to the diaphragm is as follows: the cover has a plug-in connection or threaded connection to the diaphragm. Thus, the structure is simple, and it is convenient for assembly and disassembly.

Preferably, the structure of the pipe is as follows: the top port of the pipe faces the housing on the front side of the pipe;

- a mounting chamber is defined inside the receiving chamber of the pipe and between the top port and the middle port for receiving the diaphragm;
- the diaphragm is removably mounted inside the mounting chamber of the pipe through the top port, the diaphragm is cuboidal in shape with two opposite rounded faces and has an opening facing forward and a rounded cap opposite the opening;
- a portion of the receiving chamber located between the mounting chamber and the middle port extends vertically and is opposite to a bottom wall of the diaphragm.

Under this design, it is convenient to position the diaphragm by arranging the mounting chamber. The diaphragm is relatively large in size, so it is advantageous to improve the pumping effect of the breast pump. The diaphragm is cuboidal in shape with two opposite rounded faces, so that an upper space in the milk container can be fully utilized.

Preferably, the fitting structure of the cover and the diaphragm is as follows: the opening of the diaphragm has an edge which extends out of the pipe forming a bent portion surrounding the front side of the pipe;

- the vent pipe resists against the bent portion of the diaphragm when vertically disposed;
- the cover has an insertion portion extending backward from a bottom of the vent pipe, the insertion portion is inserted into the opening of the diaphragm, so that the air chamber is enclosed by the cover and the diaphragm;
- the diaphragm further has a hook portion extending backward from the bent portion, and the hook portion clamps to the periphery of the pipe.

Under this design, by arranging the insertion portion, the cover is sealed to the diaphragm. Meanwhile, the vent pipe resists against the bent portion, so it is further advantageous for the sealing of the cover body and the diaphragm. In addition, by arranging the hook portion, it is convenient to mount the diaphragm.

Preferably, the fitting structure of the vent pipe and the air pump is as follows: the milk container has a vertical column in communication with the storing chamber;

a sealing sleeve has an upper end and a lower end, the upper end of the sealing sleeve passes through the column to be sleeved outside an output end of the air pump and the lower end thereof is removably sleeved outside a periphery of the vent pipe, the sealing sleeve is sealed to a wall of the column and the vent pipe, respectively, and an edge of the lower end of the sealing sleeve resists against the hook portion.

By arranging the sealing sleeve, the following effects are ensured. Firstly, it is advantageous for the sealing fit between the output end of the air pump and the vent pipe, avoiding air leakage. Secondly, when the breast pumping system is used and the opening of the milk container faces upward, the milk will not enter the housing. Thirdly, the vent pipe can be manufactured smaller in size, the force required to disassemble the vent pipe is smaller, so that it is convenient for the user to disassemble. Fourthly, the vent pipe can be manufactured smaller, it is not easy to cause air leakage, and the reliability is higher. The sealing sleeve resists against the hook portion, so that the hook portion is not easily separated from the pipe, and it is convenient to mount the diaphragm on the pipe.

In order to facilitate the mounting and positioning of the housing and make the space of the milk container larger, preferably, an upper wall of the storing chamber of the milk container extends upward forming a positioning portion, a bottom of the housing has a recess being sleeved on a periphery of the positioning portion;

the mounting chamber of the pipe is located inside the storing chamber in the space defined by the positioning portion.

Under this design, by arranging the positioning portion and the recess, it is convenient to mount the housing on the milk container. Moreover, the milk container can be manufactured larger, and then the accommodating space of the storing chamber is enlarged.

For achieving the second object, preferably, the pipe is an integral piece, and the passage of the shield is inserted hermetically into the middle port of the pipe.

Under this design, the pipe is an integral piece, so that the pipe will not cause air leakage. In addition, the passage of the shield is inserted hermetically into the pipe, so that it is convenient for the abutment of the both, thereby realizing easy operation, good sealing effect, difficult air leakage and good pumping effect.

In order to facilitate the mounting of the shield, preferably, the milk container has a front side and a rear side, the rear side of the milk container extends upward to form a mounting plate located on the rear side of the housing, and the shield is removably and hermetically connected to the mounting plate and the opening of the milk container. By arranging the mounting plate, it is convenient to mount the shield.

In order to reduce the size of the breast pumping system, the air pump comprises:

a pumping housing having an accommodating chamber, an air inlet, an air outlet and a pressure relief port;

a motor located outside the pumping housing;

a one-way valve;

an eccentric wheel; and a ball;

wherein, the air inlet, the air outlet and the pressure relief port communicate with the pumping housing, respectively, and are arranged at regular intervals, the air inlet communicates with the vent pipe of the cover;

the one-way valve is arranged at the air outlet and used to unidirectionally discharge air in the accommodating chamber outside of the pumping housing;

the eccentric wheel is arranged in the pumping housing and is in transmission connection to the motor and the one-way valve, respectively;

the ball is movable along the eccentric wheel and used to block or open the pressure relief port;

when the one-way valve discharges air unidirectionally, the ball blocks the pressure relief port under a centrifugal force of the eccentric wheel, and air in the air chamber of the diaphragm flows into the accommodating chamber through the air inlet; and when the one-way valve does not discharge air, the ball opens the pressure relief port, and air outside of the pumping housing enters the accommodating chamber through the pressure relief port, so that the air pressure in the accommodating chamber is restored to an initial state and the air pressure in the air chamber of the diaphragm is restored to an initial state.

Thus, the solenoid valve for discharging air is reduced in the air pump, and the mechanical structure is directly used for automatic air discharge and pressure relief, so that it is advantageous to reduce the size of the breast pumping system, reduce the productive cost and realize the reliability of the product. If the solenoid valve is used for pressure relief conventionally, it is necessary to additionally arrange a solenoid valve, a circuit board for controlling the solenoid valve, a pipe, etc., so that the structure is complicated, more pieces are needed, and the size is large.

Compared with the prior art, the present invention has the following advantages. By arranging the diaphragm, the cover and the like, the diaphragm and the cover forms an air chamber, and the air chamber is located in the receiving chamber of the milk container, so that the air chamber can be larger in size and the pumping effect of the breast pump can be improved.

When the air pump is an air pump with large pumping force, the pumping power can be further increased, and the pumping effect of the breast pump can be improved.

The diaphragm is directly sealed to the cover, so that the sealing effect is good, it is not easy to cause air leakage, and the structure is reasonable and reliable.

DETAILED DESCRIPTION OF THE INVENTION

Figure 1:
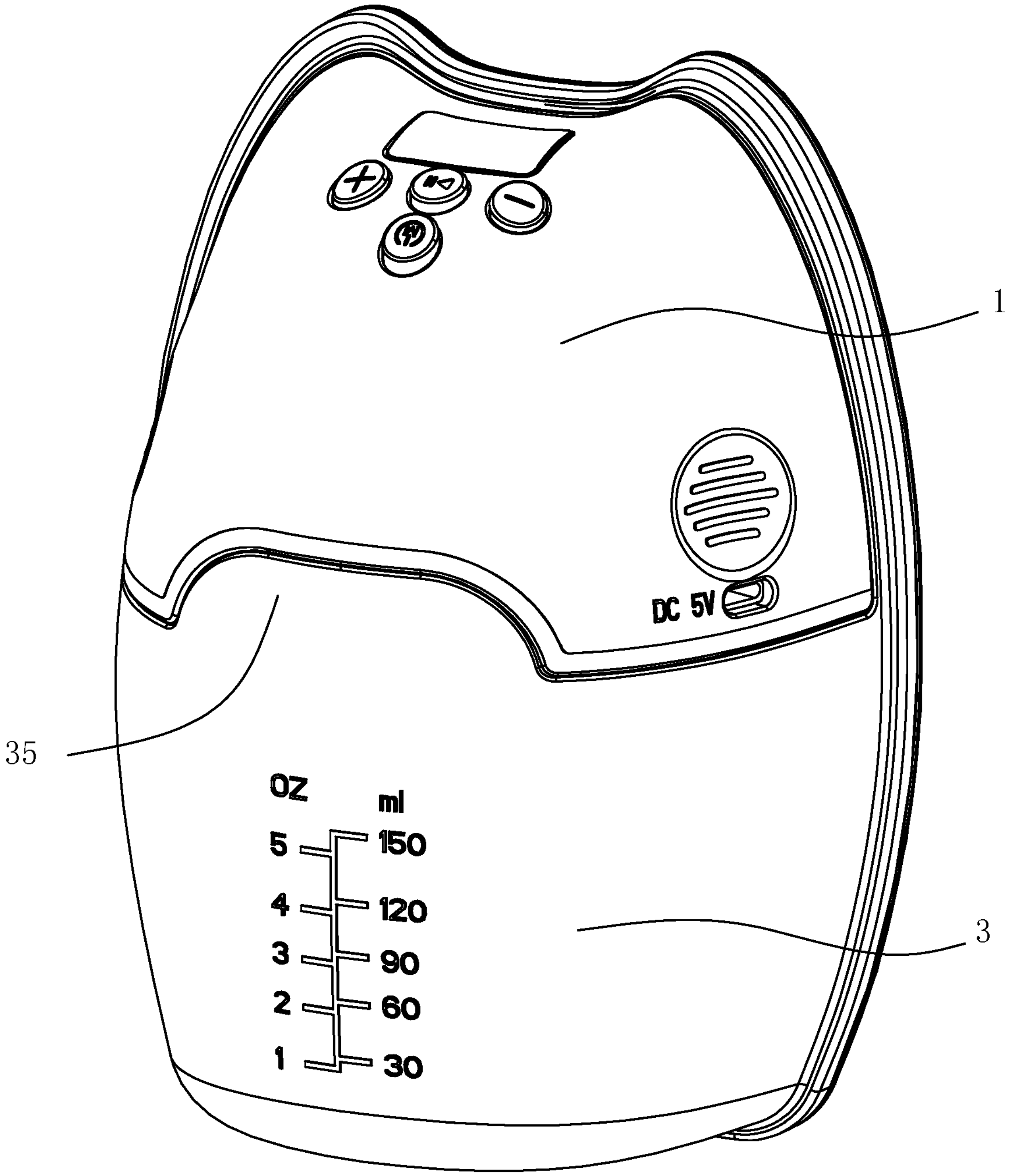
FIG. 1 is a perspective view of a breast pumping system according to an embodiment of the present invention.
Figure 2:
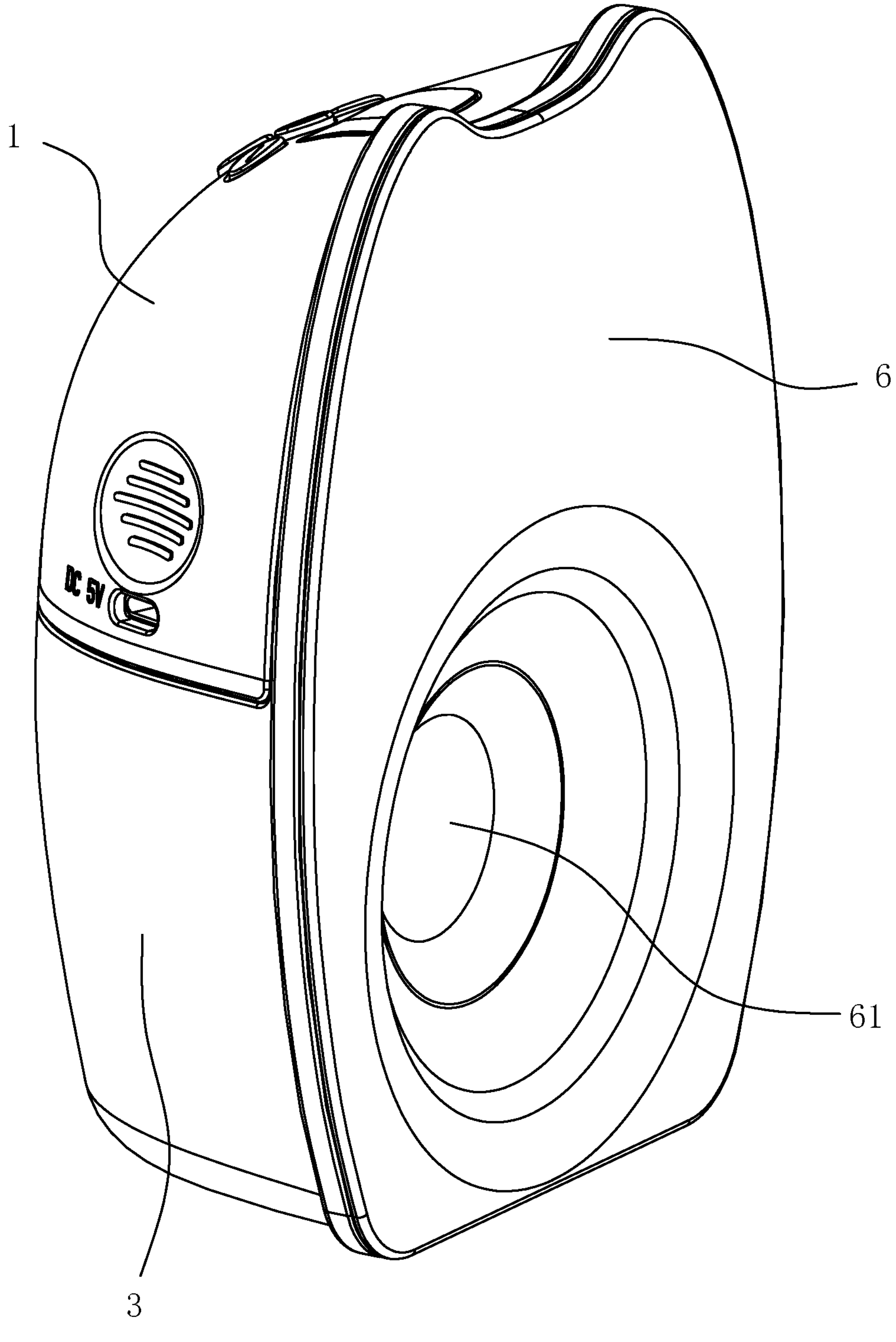
FIG. 2 is another perspective view of the breast pumping system according to the embodiment of the present invention.
Figure 3:
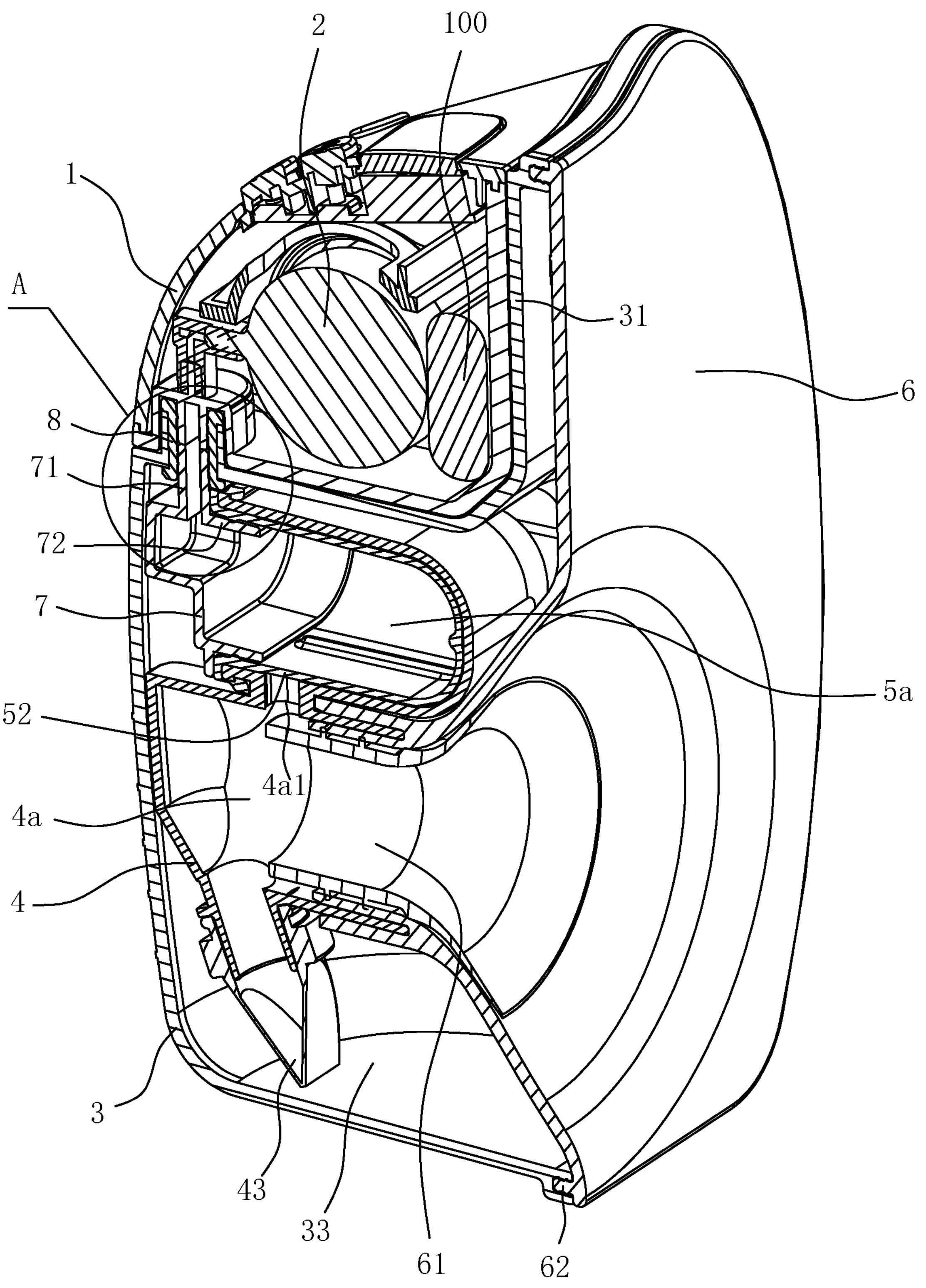
FIG. 3 is a sectional view of the breast pumping system according to the embodiment of the present invention.
Figure 4:
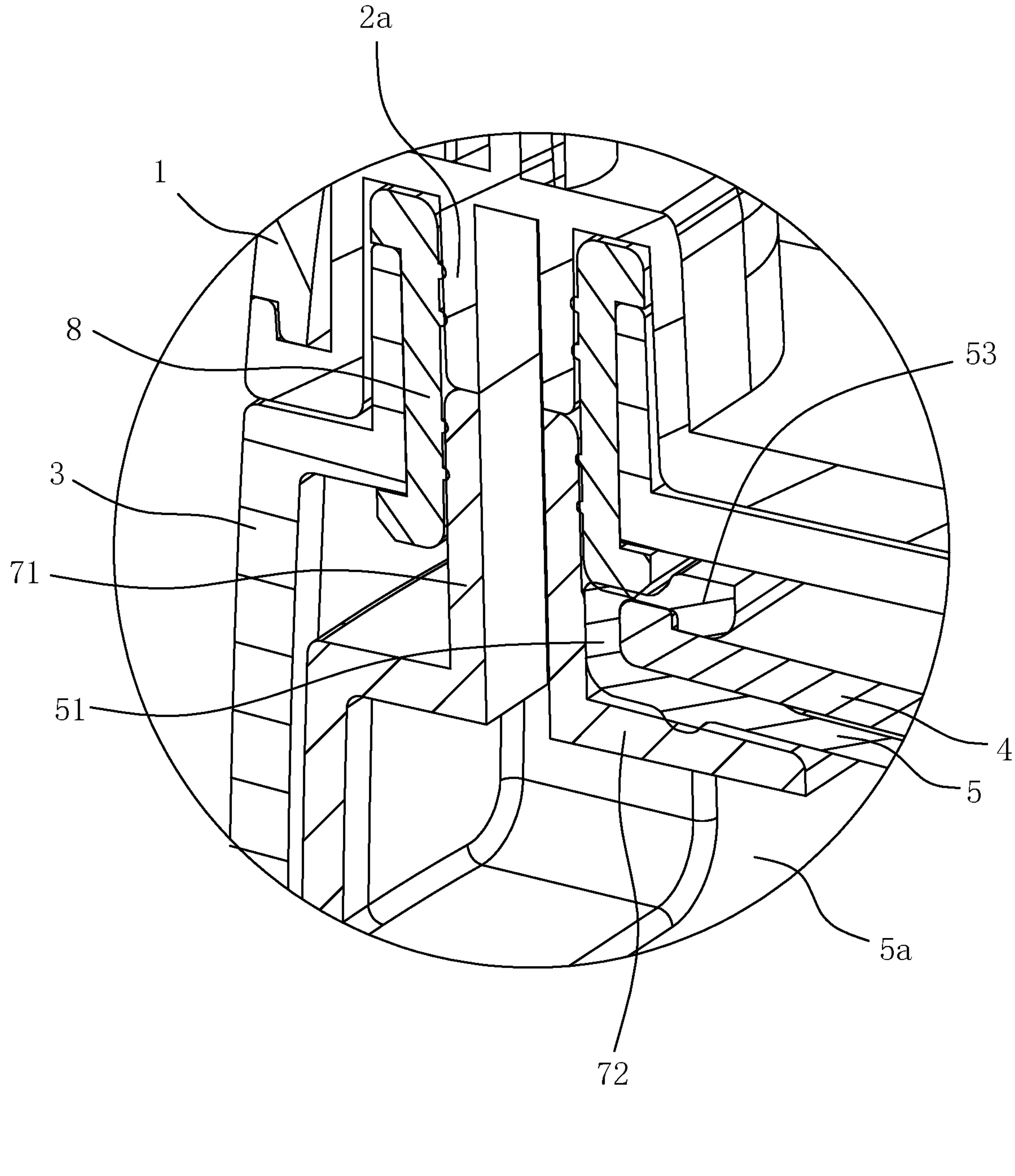
FIG. 4 is an enlarged view of Part-A in FIG. 3.
Figure 5:
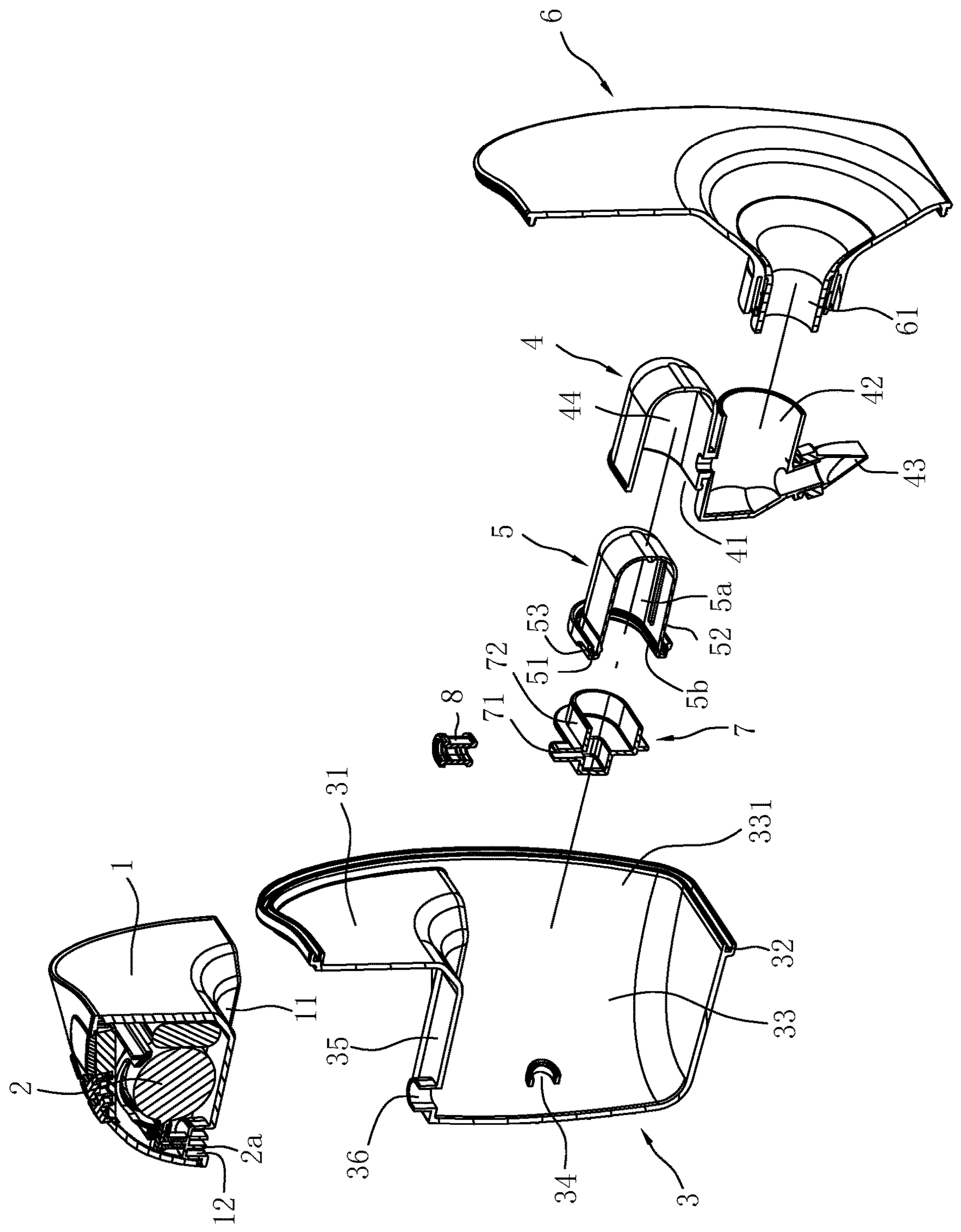
FIG. 5 is an exploded view of FIG. 3.
Figure 6:
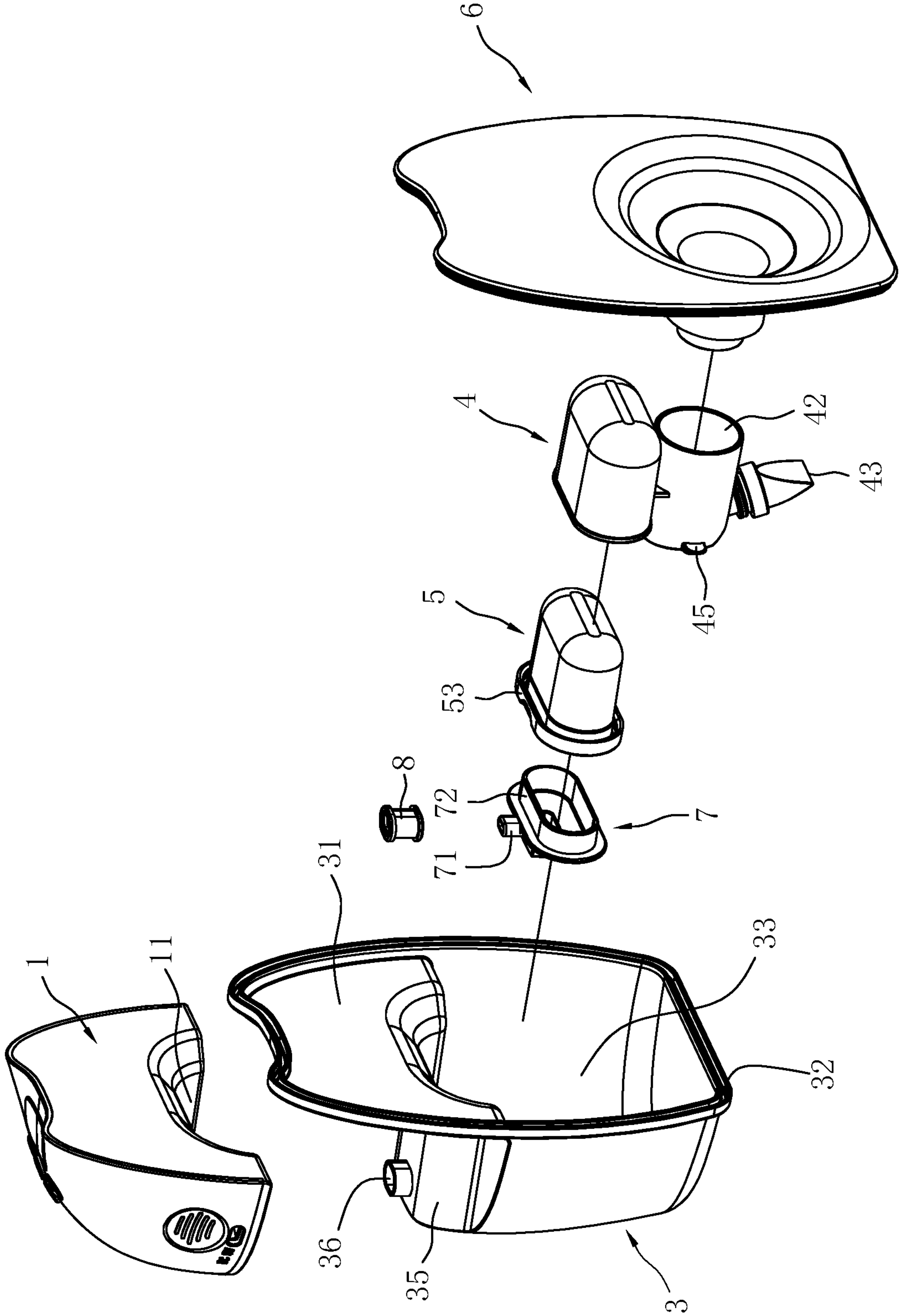
FIG. 6 is an exploded view of FIG. 2.
Figure 7:
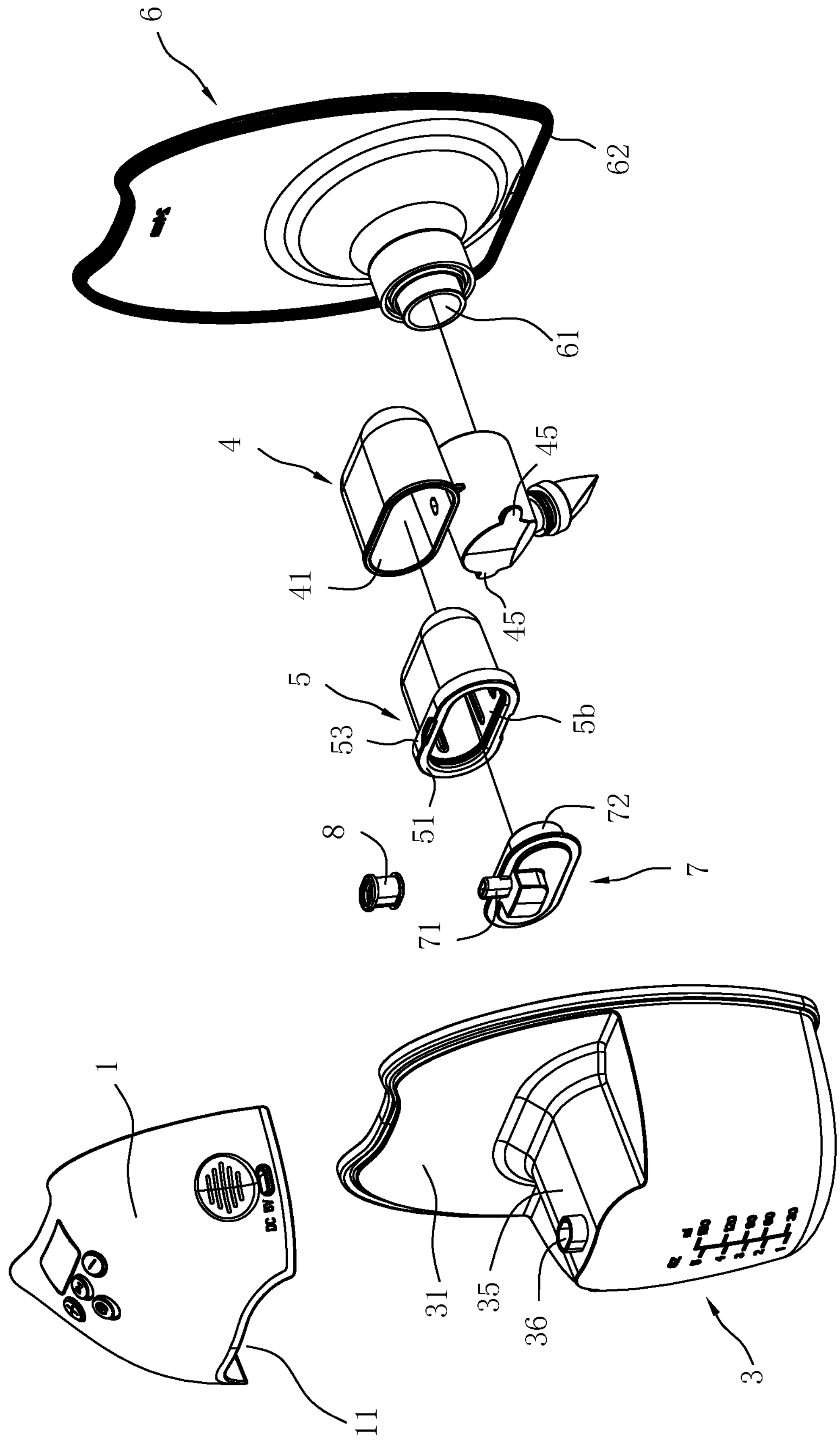
FIG. 7 is a perspective view of FIG. 6 when seen from front side.
Figure 8:
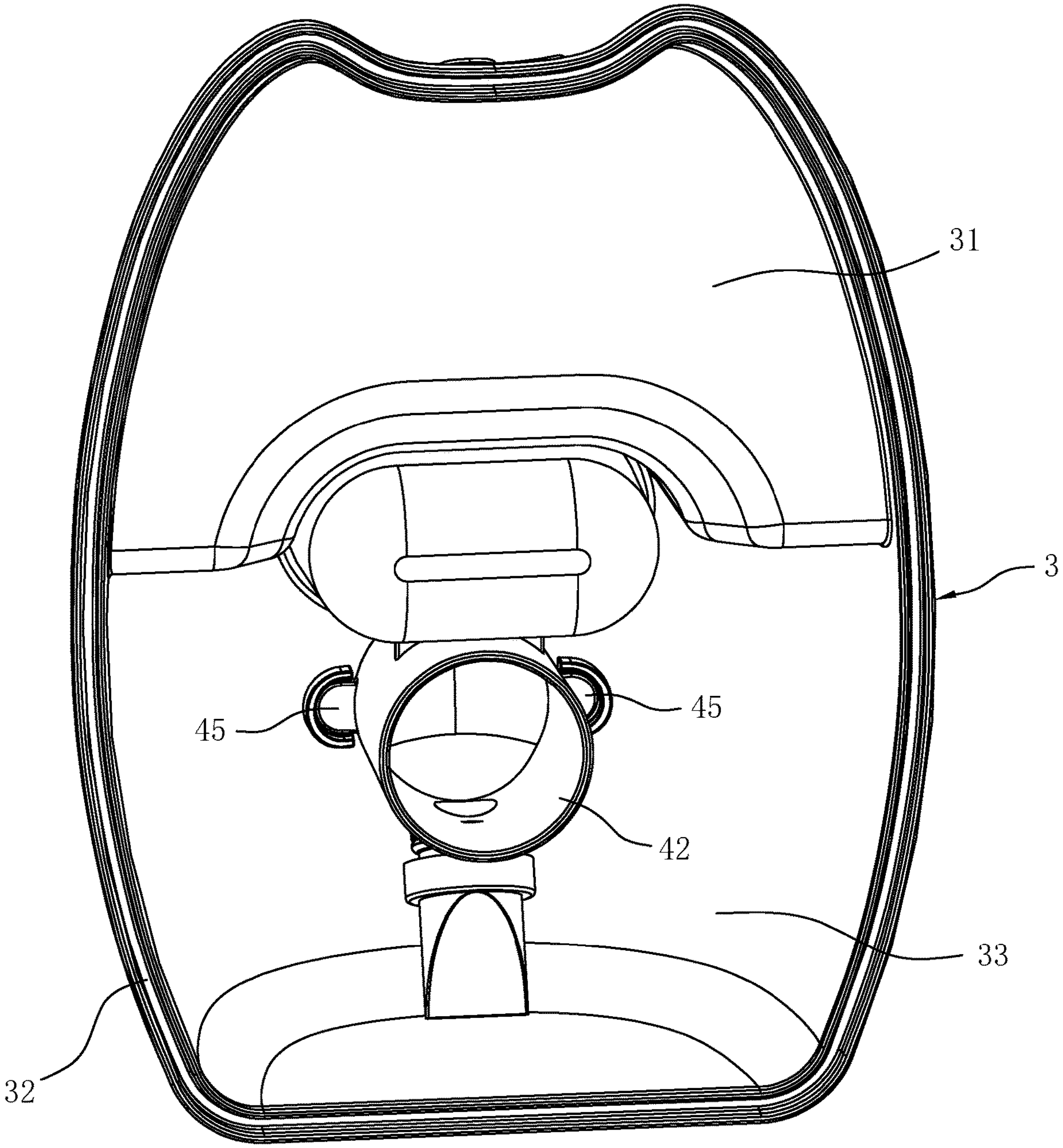
FIG. 8 is a perspective view of the breast pumping system according to the embodiment of the present invention when a shield is omitted.
Figure 9:
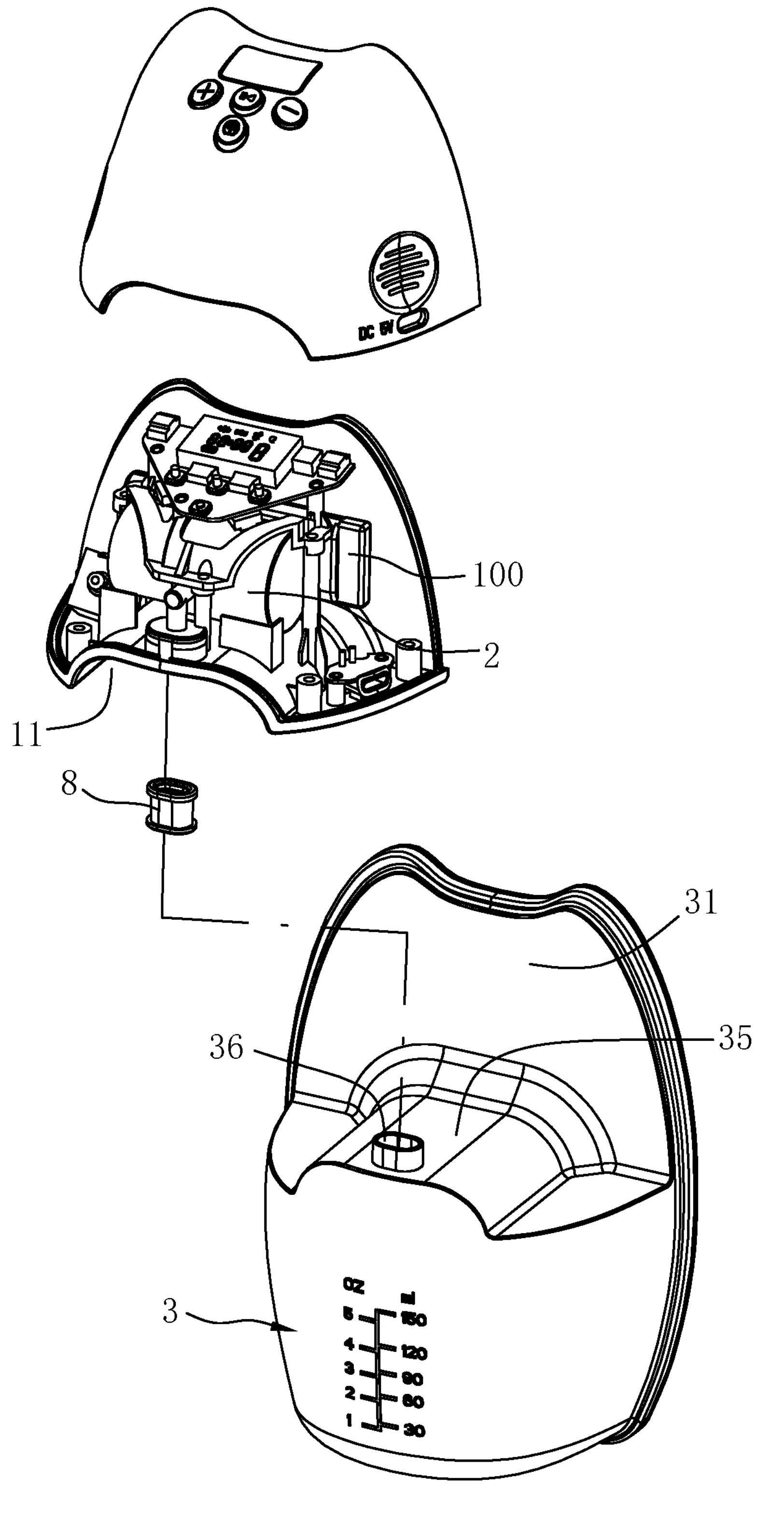
FIG. 9 is an exploded view of the breast pumping system according to the embodiment of the present invention.
Figure 10:
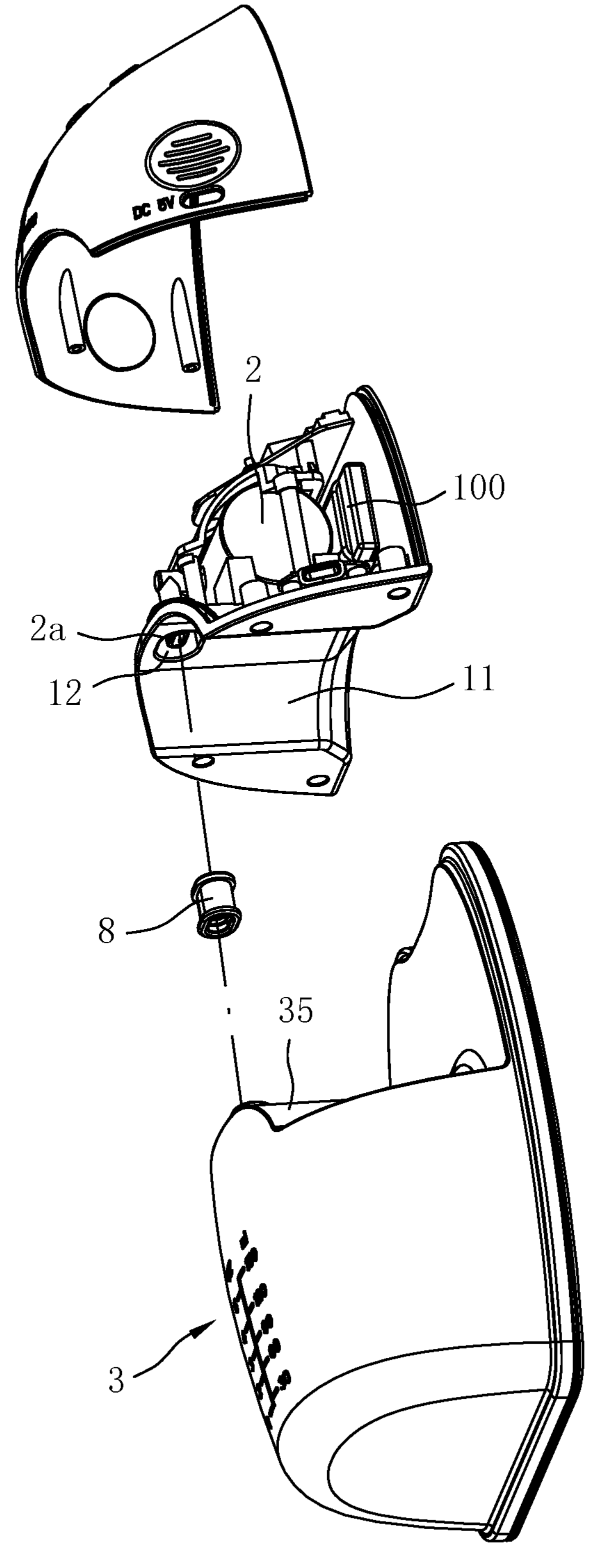
FIG. 10 is a perspective view of FIG. 9 when seen from bottom side.

The present invention will be further described below in detail by embodiments with reference to the accompanying drawings.

FIGS. 1-11 show a preferred embodiment of the breast pumping system of the present invention. The breast pumping system comprises a housing 1, an air pump 2, a milk container 3, a pipe 4, a diaphragm 5, a shield 6, a cover 7.

The housing 1 has a USB charging interface, a power button, a display screen and other conventional components on a surface of the housing 1, and a rechargeable battery 100, a circuit board or the like are disposed inside the housing 1.

Figure 11:
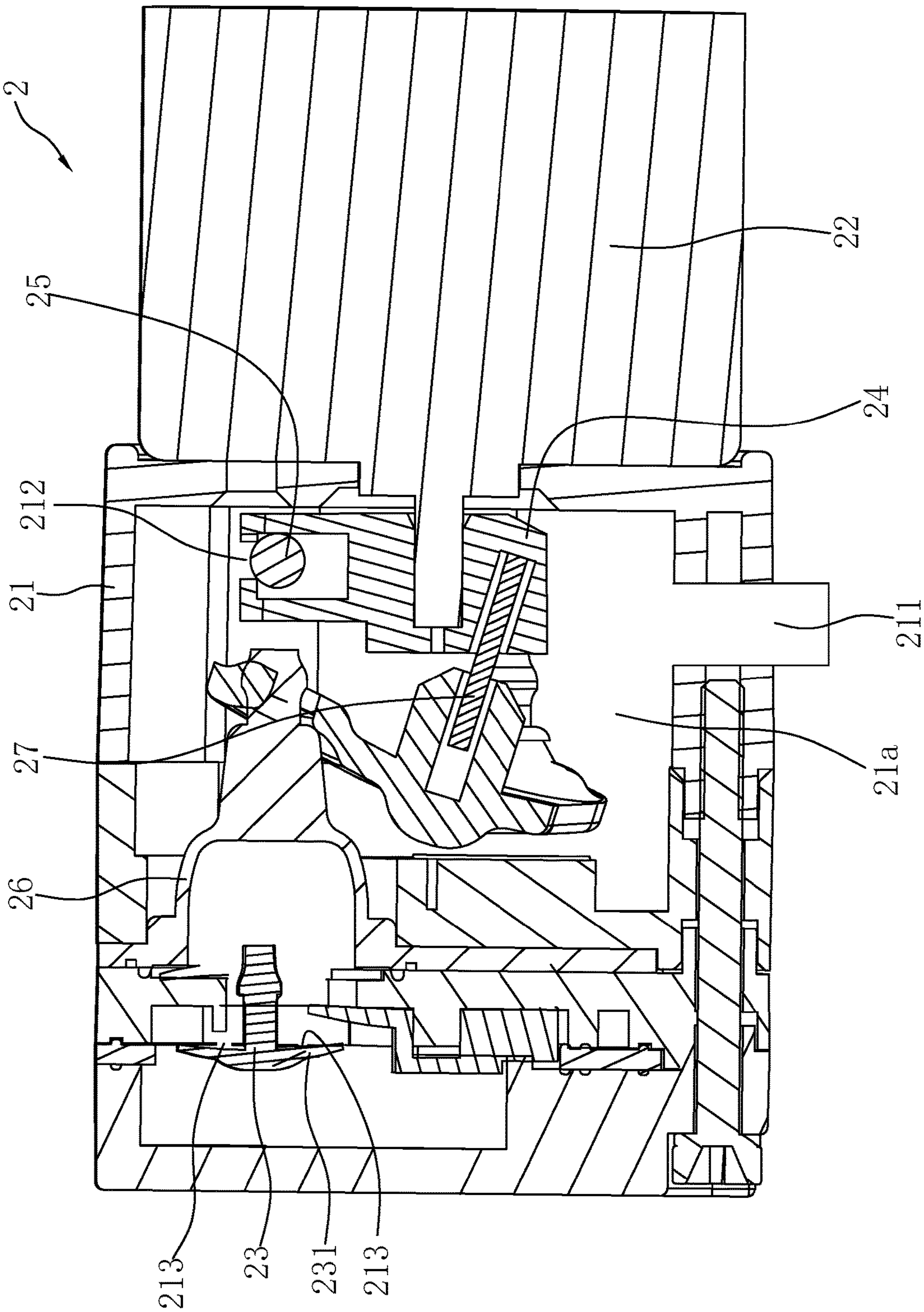
FIG. 11 is a perspective view of an air pump according to the embodiment of the present invention.

The air pump 2 is arranged inside the housing 1 and located in front of the rechargeable battery 100. With reference to FIG. 11, the air pump 2 comprises a pumping housing 21, a motor 22, a one-way valve 23, an eccentric wheel 24 and a ball 25. The pumping housing 21 has an accommodating chamber 21*a*, an air inlet 211, an air outlet 213 and a pressure relief port 212; the air inlet 211, the air outlet 213 and the pressure relief port 212 communicate with the pumping housing 21, respectively, and are arranged at regular intervals, the air inlet 211 communicates with the vent pipe 71 of the cover 7; the motor 22 located outside the pumping housing 21; the one-way valve 23 is arranged at the air outlet 213 and used to unidirectionally discharge air in the accommodating chamber 21*a* outside of the pumping housing 21; the eccentric wheel 24 is arranged in the pumping housing 21 and is in transmission connection to the motor 22 and the one-way valve 23, respectively; the ball 25 is movable along the eccentric wheel 24 and used to block or open the pressure relief port 212; when the one-way valve 23 discharges air unidirectionally, the ball 25 blocks the pressure relief port 212 under a centrifugal force of the eccentric wheel 24, and air in the air chamber 5*a* of the diaphragm 5 flows into the accommodating chamber 21*a* through the air inlet 211; and when the one-way valve 23 does not discharge air, the ball 25 opens the pressure relief port 212, and air outside of the pumping housing 21 enters the accommodating chamber 21*a* through the pressure relief port 212, so that the air pressure in the accommodating chamber 21*a* is restored to an initial state and the air pressure in the air chamber 5*a* of the diaphragm 5 is restored to an initial state. The motor 22, the eccentric wheel 24 and the one-way valve 23 adopts the structure of a diaphragm pump, so that the pumping force is larger, and it is advantageous to improve the pumping effect of the breast pumping system. Specifically, the motor 22 drives the eccentric wheel 24 to rotate, the eccentric wheel 24 drives a sway rod to rotate, so that a bowl-shaped diaphragm 26 having a bottom is stretched or compressed. The bottom of the bowl-shaped diaphragm 26 has a through hole (not shown in figures) communicating the accommodating chamber 21*a* with a bowl-shaped space of the bowl-shaped diaphragm 26, and the one-way valve 23 has a movable membrane 231. The membrane 231 is used to cover or open the air outlet 213 being communicated with the bowl-shaped diaphragm 26. When the bowl-shaped diaphragm 26 is compressed, the membrane 231 opens the air outlet 213, so that air is unidirectionally discharged to the outside of the accommodating chamber 21*a*.

The milk container 3 is detachably connected to the bottom of the housing 1, and the milk container 3 has a storing chamber 33 with a rear opening 331. An upper wall of the storing chamber 33 of the milk container 3 extends upward forming a positioning portion 35, a bottom of the housing 1 has a recess 11 being sleeved on a periphery of the positioning portion 35. In addition, the milk container 3 has vertical column 36 in communication with the storing chamber 33; a sealing sleeve 8 has an upper end and a lower end, the upper end of the sealing sleeve 8 passes through the column 36 to be sleeved outside an output end 2*a* of the air pump 2 and the lower end thereof is removably sleeved outside a periphery of the vent pipe 71, as specifically shown in FIGS. 5 and 10, the bottom of the housing 1 has a recessed cavity 12, the output end 2*a* of the air pump 2*a* extends vertically to the outside of the housing 1, the output end 2*a* is located inside the recessed cavity 12, the sealing sleeve 8 is sealed to a wall of the column 36 and the vent pipe 71, respectively. The upper end of the sealing sleeve 8 is sleeved outside the output end 2*a* of the air pump 2 and located in the recessed cavity 12, and the lower end of the sealing sleeve 8 is sleeved outside the vent pipe 71 and located inside the mounting hole 36. The inner peripheral wall of the sealing sleeve 8 has a sealing ring that extends circumferentially, so that the sealing effect is good. The sealing sleeve 8 is preferably made of a flexible material, for example, silicone, rubber, etc.

The pipe 4 is detachably arranged in the storing chamber 33 of the milk container 3. The pipe is a three-way pipe, is integrally formed, and has a front side, a receiving chamber 4*a*, a top port 41, a middle port 42 and a lower port 43, the top port 41, the middle port 42 and the lower port 43 communicating with the receiving chamber 4*a*, the middle port 42 facing backward, the lower port 43 communicating with the storing chamber 33. The structure of the lower port 43 adopts the existing structure. Specifically, the lower port 43 has a one-way valve. When a negative pressure is formed in the pipe 4, the one-way valve is closed. After the air pressure in the pipe 4 is restored, the one-way valve is opened, and the milk enters the storing chamber 33. In order to facilitate the mounting and positioning of the pipe 4, the milk container 3 has a positioning slot 34, and the pipe 4 has one or one more positioning ribs 45 extending into the positioning slot 34. The positions of the positioning ribs 45 and the positioning slot 34 may be interchanged. In this embodiment, each positioning rib 45 is arranged on the left and right of the pipe 4, and the position and number of the positioning ribs may be adjusted as required.

The diaphragm 5 is arranged inside the receiving chamber 4*a* of the pipe 4 and located between the top port 41 and the middle port 42; the diaphragm 5 is at least partially distortable in shape and is capable of isolating air from the vent pipe 71 from milk inside the receiving chamber 4*a* of the pipe 4. Preferably, the whole diaphragm 5 is made of a silicone material to facilitate deformation, or may also be made of other deformable materials or structures.

The cover 7 is arranged inside the storing chamber 33 and located at the top port 41 of the pipe 4, an air chamber 5*a* being defined between the cover 7 and the diaphragm 5, the cover 7 having a vent pipe 71 communicating with the air chamber 5*a* and the air pump 2. Preferably, the cover 7 is detachably sealed to the diaphragm 5. Specifically, the cover 7 has a plug-in connection or threaded connection to the diaphragm 5.

The shield 6 has a passage 61 facing backward for receiving a nipple, the passage 61 communicating with the middle port 42 of the pipe 4, the shield 6 covering the rear opening 331 of the milk container 3. Specifically, the milk container 3 has a limiting slot 32 extending in the front-rear direction, and the shield 6 has one or one more limiting ribs 62 extending into the limiting slot 32. The positions of the limiting ribs 62 and the limiting groove 32 may be interchanged.

when the air pump 2 acts on the air chamber 5*a* through the vent pipe 71, the diaphragm 5 is distorted so as to form a negative pressure inside the receiving chamber 4*a* of the pipe 4, accordingly the milk from the passage 61 flows into the storing chamber 33 of the milk container 3 after passing through the receiving chamber 4*a* and the lower port 43 successively.

The fitting structure of the pipe 4, the diaphragm 5 and the cover 7 is specifically described below.

The top port 41 of the pipe 4 faces the housing 1 on the front side of the pipe 4; a mounting chamber 44 is defined inside the receiving chamber 4*a* of the pipe 4 and between the top port 41 and the middle port 42 for receiving the diaphragm 5; the diaphragm 5 is removably mounted inside the mounting chamber 44 of the pipe 4 through the top port 41, the diaphragm 5 is cuboidal in shape with two opposite rounded faces and has an opening 5*b* facing forward and a rounded cap opposite the opening 5*b*. The mounting chamber 44 of the pipe 4 is located inside the storing chamber 33 in the space defined by the positioning portion 35. A portion 4*al* of the receiving chamber 4*a* located between the mounting chamber 44 and the middle port 42 extends vertically and is opposite to a bottom wall of the diaphragm 5. The opening 5*b* of the diaphragm 5 has an edge which extends out of the pipe 4 forming a bent portion 51 surrounding the front side of the pipe 4; the vent pipe 71 resists against the bent portion 51 of the diaphragm 5 when vertically disposed; the cover 7 has an insertion portion 72 extending backward from a bottom of the vent pipe 71, the insertion portion 72 is inserted into the opening 5*b* of the diaphragm 5, so that the air chamber 5*a* is enclosed by the cover 7 and the diaphragm 5; the diaphragm 5 further has a hook portion 53 extending backward from the bent portion 51, and the hook portion 53 clamps to the periphery of the pipe 4, and the hook portion 53 resists against an edge of the lower end of the sealing sleeve 8. During mounting, the hook portion 53 of the diaphragm 5 clamps to the outer wall of the pipe 4, and then the diaphragm 5 is connected to the cover 7.

The operation principle will be described below.

The breast pumping system is placed in a bra, the nipple of the user is placed in the nipple passage 61, and the shield 6 attaches to the breast, so that the breast pumping system can be worn independently and is hand-free and easy to use.

The air pump 2 is powered on to suck air, and the diaphragm 5 is deformed, so that negative pressure is formed in the receiving chamber 4*a* of the pipe 4, and milk enters the storing chamber 33 of the milk container 3 after successively passing through the nipple passage 61, the receiving chamber 4*a* and the lower port 43 under the action of the negative pressure and the gravity. In addition, the air pump 2 adopts a mechanical structure for automatic air discharge and pressure relief, so that it is advantageous to reduce the size of the breast pumping system. The operation process of the air pump 2 is specifically described below. The motor 22 operates to drive the one-way valve 23 to discharge air to the outside of the pumping housing 21, negative pressure is then formed in the accommodating chamber 21*a*, and the air in the air chamber 5*a* of the diaphragm 5 enters the accommodating chamber 21*a* of the air pump 2. Meanwhile, the ball 25 blocks the pressure relief port 212 under the centrifugal force. When the ball 5 does not block the pressure relief port 212, the air outside the pumping housing 21 enters the accommodating chamber 21*a* through the pressure relief port 212, so that the pressure in the accommodating chamber 21*a* is restored to the initial pressure, and the pressure in air chamber 5*a* of the diaphragm 5 is also restored to the initial pressure.

The air pump 2 operates continuously, so that the diaphragm 5 reciprocates between deformation and restoration to the original state, and milk is continuously pumped into the milk container 3.

The diaphragm 5 completely isolates the air from the air pump 2 from the milk in the receiving chamber 4 of the pipe 4, so that the milk will not be polluted.

After the air pump 2 is powered off, the air pump 2 is automatically deflated and restored to the original state.

The milk container 3, the pipe 4, the diaphragm 5, the cover 7 and the shield 6 all can be disassembled from the breast pumping system, so that these components are convenient for cleaning, disinfection, and replacement of new parts, etc.

The invention claimed is:

1. A breast pumping system, comprising:

a housing having a lower portion, a front side and a rear side;

an air pump arranged inside the housing;

a milk container arranged at the lower portion of the housing, having a storing chamber with a rear opening;

a pipe arranged inside the storing chamber of the milk container, having a front side, a receiving chamber, a top port, a middle port and a lower port, the top port, the middle port and the lower port communicating with the receiving chamber, the middle port facing backward, the lower port communicating with the storing chamber;

a diaphragm arranged inside the receiving chamber of the pipe and located between the top port and the middle port;

a shield having a passage facing backward for receiving a nipple, the passage communicating with the middle port of the pipe, the shield covering the rear opening of the milk container;

a cover arranged inside the storing chamber and located at the top port of the pipe, an air chamber being defined between the cover and the diaphragm, the cover having a vent pipe communicating with the air chamber and the air pump;

wherein, the diaphragm has an opening and is at least partially distortable in shape and is capable of isolating air from the vent pipe from milk inside the receiving chamber of the pipe;

when the air pump acts on the air chamber through the vent pipe, the diaphragm is distorted so as to form a negative pressure inside the receiving chamber of the pipe, accordingly the milk from the passage flows into the storing chamber of the milk container after passing through the receiving chamber and the lower port successively;

the cover is detachably sealed to the diaphragm;

the opening of the diaphragm has an edge which extends out of the pipe forming a bent portion surrounding the front side of the pipe;

the vent pipe presses against the bent portion of the diaphragm when vertically disposed;

the cover has an insertion portion extending backward from a bottom of the vent pipe, the insertion portion is inserted into the opening of the diaphragm, so that the air chamber is enclosed by the cover and the diaphragm;

the diaphragm further has a hook portion extending backward from the bent portion, and the hook potion clamps to the periphery of the pipe the milk container has a vertical column in communication with the storing chamber;

a sealing sleeve has an upper end and a lower end, the upper end of the sealing sleeve passes through the column to be sleeved outside an output end of the air pump and the lower end thereof is removably sleeved outside a periphery of the vent pipe, the sealing sleeve is sealed to a wall of the column and the vent pipe, respectively, and an edge of the lower end of the sealing sleeve presses against the hook portion.

2. The breast pumping system of claim 1, wherein the cover has a plug-in connection or threaded connection to the diaphragm.

3. The breast pumping system of claim 1, wherein the top port of the pipe faces the housing on the front side of the pipe;

a mounting chamber is defined inside the receiving chamber of the pipe and between the top port and the middle port for receiving the diaphragm;

the diaphragm is removably mounted inside the mounting chamber of the pipe through the top port, the diaphragm is cuboidal in shape with two opposite rounded faces; the opening of the diaphragm faces forward and a rounded cap faces opposite the opening;

a portion of the receiving chamber located between the mounting chamber and the middle port extends vertically and is opposite to a bottom wall of the diaphragm.

4. The breast pumping system of claim 3, wherein an upper wall of the storing chamber of the milk container extends upward forming a positioning portion, a bottom of the housing has a recess being sleeved on a periphery of the positioning portion;

the mounting chamber of the pipe is located inside the storing chamber in the space defined by the positioning portion.

5. The breast pumping system of claim 1, wherein the pipe is an integral piece, and the passage of the shield is inserted hermetically into the middle port of the pipe.

6. The breast pumping system of claim 1, wherein the milk container has a front side and a rear side, the rear side of the milk container extends upward to form a mounting plate located on the rear side of the housing, and the shield is removably and hermetically connected to the mounting plate and the opening of the milk container.

7. The breast pumping system of claim 1, wherein the air pump comprises:

a pumping housing having an accommodating chamber, an air inlet, an air outlet and a pressure relief port;

a motor located outside the pumping housing;

a one-way valve;

an eccentric wheel; and a ball;

wherein, the air inlet, the air outlet and the pressure relief port communicate with the pumping housing, respectively, and are arranged at regular intervals, the air inlet communicates with the vent pipe of the cover;

the one-way valve is arranged at the air outlet and used to unidirectionally discharge air in the accommodating chamber outside of the pumping housing;

the eccentric wheel is arranged in the pumping housing and is in transmission connection to the motor and the one-way valve, respectively;

the ball is movable along the eccentric wheel and used to block or open the pressure relief port;

when the one-way valve discharges air unidirectionally, the ball blocks the pressure relief port under a centrifugal force of the eccentric wheel, and air in the air chamber of the diaphragm flows into the accommodating chamber through the air inlet; and when the one-way valve does not discharge air, the ball opens the pressure relief port, and air outside of the pumping housing enters the accommodating chamber through the pressure relief port, so that the air pressure in the accommodating chamber is restored to an initial state and the air pressure in the air chamber of the diaphragm is restored to an initial state.

* * * * *